(12) United States Patent
Souza et al.

(10) Patent No.: US 9,181,152 B2
(45) Date of Patent: Nov. 10, 2015

(54) PROCESS FOR PREPARATION OF (3R)-2,4-DI-LEAVING GROUP-3-METHYLBUT-1-ENE

(71) Applicant: ALPHORA RESEARCH INC., Mississauga (CA)

(72) Inventors: Fabio E. S. Souza, Mississauga (CA); Huzaifa Rangwala, Mississauga (CA); Boris Gorin, Oakville (CA); Ming Pan, Mississauga (CA)

(73) Assignee: ALPHORA RESEARCH INC., Mississauga (CA)

( * ) Notice: Subject to any disclaimer, the term of this patent is extended or adjusted under 35 U.S.C. 154(b) by 0 days.

(21) Appl. No.: 14/361,489

(22) PCT Filed: Nov. 29, 2012

(86) PCT No.: PCT/CA2012/050859
§ 371 (c)(1),
(2) Date: May 29, 2014

(87) PCT Pub. No.: WO2013/078559
PCT Pub. Date: Jun. 6, 2013

(65) Prior Publication Data
US 2014/0323744 A1 Oct. 30, 2014

Related U.S. Application Data

(60) Provisional application No. 61/565,094, filed on Nov. 30, 2011.

(51) Int. Cl.
| | |
|---|---|
| *C07C 17/16* | (2006.01) |
| *C07C 309/73* | (2006.01) |
| *C07D 493/22* | (2006.01) |
| *C07C 309/65* | (2006.01) |
| *C07C 309/66* | (2006.01) |
| *C07C 17/093* | (2006.01) |
| *C07C 21/14* | (2006.01) |
| *C07C 21/17* | (2006.01) |
| *C07C 29/09* | (2006.01) |
| *C07D 407/14* | (2006.01) |

(52) U.S. Cl.
CPC .............. *C07C 17/16* (2013.01); *C07C 17/093* (2013.01); *C07C 21/14* (2013.01); *C07C 21/17* (2013.01); *C07C 29/09* (2013.01); *C07C 309/65* (2013.01); *C07C 309/66* (2013.01); *C07C 309/73* (2013.01); *C07D 407/14* (2013.01); *C07D 493/22* (2013.01); *C07B 2200/07* (2013.01)

(58) Field of Classification Search
CPC ........................................................ C07C 17/16
USPC ......................................................... 549/344
See application file for complete search history.

(56) References Cited

U.S. PATENT DOCUMENTS

| | | | |
|---|---|---|---|
| 5,436,238 | A | 7/1995 | Kishi et al. |
| 6,214,865 | B1 | 4/2001 | Littlefield et al. |
| 2004/0192885 | A1 | 9/2004 | Sharma et al. |

FOREIGN PATENT DOCUMENTS

| | | |
|---|---|---|
| CA | 2166898 | 9/2004 |
| WO | 93/17690 | 9/1993 |
| WO | 99/65894 | 12/1999 |
| WO | 2005118565 | 12/2005 |
| WO | 2009/124237 | 10/2009 |
| WO | 2013/086634 | 6/2013 |
| WO | 2013/097042 | 7/2013 |
| WO | 2013/142999 | 10/2013 |
| WO | 2014/183211 | 11/2014 |

OTHER PUBLICATIONS

Choi et al., "Synthetic studies on the marine natural product halichondrins", Pure Appl. Chem., vol. 75, No. 1, pp. 1-17, 2003, Massachusetts (CHOI_ET_AL_1).
Choi et al., "Asymmetric Ni(II)/Cr(II)-Mediated Coupling Reaction: Catalytic Process", Organic Letters, vol. 4, No. 25, pp. 4435-4438, 2002, Massachusetts (CHOI_ET_AL_2).
Cook et al., "Total Synthesis of (−)-Exiguolide", Organic Letters, vol. 12, No. 4, pp. 744-747, 2010, France.
Dong et al., "New Syntheses of E7389 C14-C35 and Halichondrin C14-C38 Building Blocks: Reductive Cyclization and Oxy-Michael Cyclization Approaches", J. Am. Chem. Soc., vol. 131, pp. 15642-15646, 2009, Massachusetts.
Guo et al., "Toolbox Approach to the Search for Effective Ligands for Catalytic Asymmetric Cr-Mediated Coupling Reactions", J. Am. Chem. Soc., vol. 131, pp. 15387-15393, 2009, Massachusetts.
Han et al., "Iridium-Catalyzed anti-Diastereo- and Enantioselective Carbonyl (Trimethylsilyl)allylation from the Alcohol of Aldehyde Oxidation Level", J. Am. Chem. Soc., vol. 132, pp. 9153-9156, 2010, Texas (HAN_ET_AL_1).
Han et al., Supporting Information to "Iridium-Catalyzed anti-Diastereo- and Enantioselective Carbonyl (Trimethylsilyl) allylation from the Alcohol of Aldehyde Oxidation Level", J. Am. Chem. Soc., vol. 132, pp. 9153-9156, 2010, Texas (HAN_ET_AL_2).

(Continued)

*Primary Examiner* — Taofiq A Solola
(74) *Attorney, Agent, or Firm* — Grossman, Tucker, Perreault & Pfleger, PLLC

(57) ABSTRACT

The specification relates to compounds and process for the preparation of a compound of formula 7,

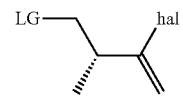

where LG is a leaving group and hal is a halide and is Cl, Br or I. The compound of formula 7 can be useful in the preparation of natural products, such as halichondrin and its derivatives.

22 Claims, No Drawings

(56) References Cited

OTHER PUBLICATIONS

Jackson et al., "A Total Synthesis of Norhalichondrin B", Angewandte Chemie, vol. 48, No. 13, pp. 1-132, 2009, Colorado (JACKSON_ET_AL_1).

Jackson et al., "The Halichondrins and E7389", Chem. Rev., vol. 109, pp. 3044-3079, 2009, Colorado (JACKSON_ET_AL_2).

Jiang et al., "A Practical Synthesis of the F-Ring of Halichondrin B via Ozonolytic Desymmetrization of C2-Symmetric Dihydroxycyclohexene", J. Org. Chem., vol. 68, pp. 1150-1153, 2003, Wisconsin (JIANG_ET_AL_1).

Jiang et al., "A Novel Route to the F-Ring of Halichondrin B. Diastereoselection in Pd(0)-Mediated meso and C2 Diol Desymmetrization", Organic Letters, vol. 4, No. 20, pp. 3411-3414, 2002, Wisconsin (JIANG_ET_AL_2).

Kim et al., "New Syntheses of E7389 C14-C35 and Halichondrin C14-C38 Building Blocks: Double-Inversion Approach", J. Am. Chem. Soc., vol. 131, pp. 15636-15641, 2009, Massachusetts.

Kunznetsov et al., "Induction of Morphological and Biochemical Apoptosis following Prolonged Mitotic Blockage by Halichondrin B Macrocyclic Ketone Analog E7389", Cancer Research, vol. 64, pp. 5760-5766, 2004, Japan.

Litaudon et al., "Isohomoalichondrin B, a New Antitumour Polyether Macrolide from the New Zealand Deep-Water Sponge Lissodendoryx sp.", Tetrahedron Letters, vol. 35, No. 50, pp. 9435-9438, 1994, New Zealand.

Narayan et al., "Novel second generation analogs of eribulin. Part I: Compounds containing a lipophilic C32 side chain overcome P-glycoprotein susceptibility", Bioorganic & Medicinal Chemistry Letters, vol. 21, pp. 1630-1633, 2011, Massachusetts (NARAYAN_ET_AL_1).

Narayan et al., "Novel second generation analogs of eribulin. Part II: Orally available and active against resistant tumors in vivo", Bioorganic & Medicinal Chemistry Letters, vol. 21, pp. 1634-1638, 2011, Massachusetts (NARAYAN_ET_AL_2).

Narayan et al., "Novel second generation analogs of eribulin. Part III: Blood-brain barrier permeability and in vivo activity in a brain tumor model", Bioorganic & Medicinal Chemistry Letters, vol. 21, pp. 1639-1643, 2011, Massachusetts (NARAYAN_ET_AL_3).

Okouneva et al., "Inhibition of centromere dynamics by eribulin (E7389) during mitotic metaphase", Mol. Cancer Ther., vol. 7, No. 7, pp. 2003-2011, 2008, California.

Rudolph et al., "Early introduction of the amino group to the C27-C35 building block of Eribulin", Tetrahedron Letters, vol. 54, pp. 7059-7061, 2013, Canada.

Sabitha et al., "Synthesis of the C45-053 tetrahydropyran domain of norhalichondrins and the C14-C22 tetrahydrofuran domain of the halichondrin family", RSC Advances, vol. 2, pp. 10157-10159, 2012, India.

Sartillo-Piscil et al., "Diastereoselective synthesis of 1,2-O-isopropylidene-1,6-dioxaspiro[4,4]nonane applying the methodology of generation of radical cations under non-oxidizing conditions", Tetrahedron Letters, vol. 44, pp. 3919-3921, 2003, Mexico.

Sun et al., "Synthesis and Olefination Reactions of an a-Enal from Diacetone Glucose", Communications Synthesis, pp. 28-29, 1982, Maryland.

Trost et al., "Ru-Catalyzed Alkene-Alkyne Coupling. Total Synthesis of Amphidinolide P", J. Am. Chem. Soc., vol. 127, pp. 17921-17937, 2005, California.

Wang et al., "Structure-Activity Relationships of Halichondrin B Analogues: Modifications at C.30-C.38", Bioorganic & Medicinal Chemistry Letters, vol. 10, pp. 1029-1032, 2000, Massachusetts.

Zheng et al., "Macrocyclic ketone analogues of halichondrin B", Bioorganic & Medicinal Chemistry Letters, vol. 14, pp. 5551-5554, 2004, Massachusetts.

International Search Report and Written Opinion from corresponding PCT Appln. No. PCT/CA2012/050859, dated Jan. 29, 2013.

International Search Report and Written Opinion from related PCT Appln. No. PCT/CA2012/050939, dated Feb. 15, 2013.

International Search Report and Written Opinion from related PCT Appln. No. PCT/CA2012/050254, dated Jul. 8, 2013.

International Preliminary Report on Patentability from related PCT Appln. No. PCT/CA2012/050897, dated Jun. 17, 2014.

International Preliminary Report on Patentability from related PCT Appln. No. PCT/CA2012/050939, dated Jul. 1, 2014.

International Search Report from related PCT Appln. No. PCT/CA2012/050504, dated Jul. 24, 2014.

International Search Report and Written Opinion from related PCT Appln. No. PCT/CA2012/050438, dated Jul. 25, 2014.

PROCESS FOR PREPARATION OF (3R)-2,4-DI-LEAVING GROUP-3-METHYLBUT-1-ENE

CROSS-REFERENCE TO RELATED APPLICATION

This application claims the benefit of and priority to U.S. Provisional patent application No. 61/565,094, filed Nov. 30, 2011. The content of the above-noted patent application is hereby expressly incorporated by reference into the detailed description hereof.

FIELD

This specification relates to a process for the preparation of (3R)-2,4-di-leaving group-3-methylbut-1-ene, and intermediates thereof.

BACKGROUND

Halinchondrin analogs have been disclosed as having anticancer and antimitotic activity (U.S. Pat. No. 6,214,865, incorporated herein by reference). In particular, Halichondrin B has been reported as a potent anticancer agent that was first isolated from the marine sponge Halichondria okadai (U.S. Pat. No. 6,214,865; WO 2005/118565 A1 and WO 2009/124237 A1, all incorporated herein by reference).

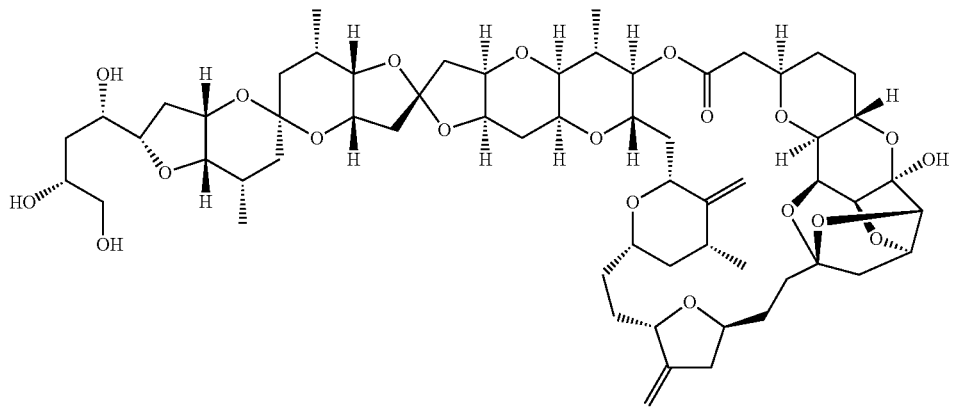

Halichondrin B (3R)-2,4-diiodo-3-methylbut-1-ene (7a) has been disclosed as a building block in the synthesis of halichondrin natural products and derivatives ((1)(a) Katrina, L. et al., *Angewandte Chemie, International Edition*, 2009, v. 48, no. 13, 2346-2350, (b) Kim, D-S. et al., *Journal of the American Chemical Society*, 2009, v. 131, no. 43, 15636-15641, (c) Guo, H. et al., *Journal of the American Chemical Society*, 2009, v. 131, no. 42, 15387-15393, (d) Choi, H-w. et al. *Organic Letters*, 2002, v. 4, no. 25, 4435-4438, all incorporated herein by reference). The preparation of (3R)-2,4-diiodo-3-methylbut-1-ene (7a) has been disclosed by two synthetic methods,[1b] both of which can be unsuitable for large scale manufacturing of pharmaceutical quality material. The first approach involves the asymmetric SN2' reaction of a cuprate. In addition to the difficulties that can be inherent to cuprate chemistry, the product is isolated in 98% enantiomeric excess (e.e.), with its enantiomer present in levels well above the 0.10% that can generally be required by regulatory agencies. The second method involves the use of trimethylaluminum, a pyrophoric chemical, which can pose a significant hazard for large scale reaction.

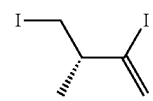

There is a need in the art for a process for preparation of (3R)-2,4-diiodo-3-methylbut-1-ene (7a), and its analogs (7), that can be used in the preparation of halichondrin natural products, its derivatives and analogs, such as, for example and without limitation, eribulin the compounds described in recent publication of S. Narayan and others (*Bioorganic and Medicinal Chemistry letters*, 2011, 1630-1633; *Bioorganic and Medicinal Chemistry letters*, 2011, 1634-1638, *Bioorganic and Medicinal Chemistry letters*, 2011, 1639-1643), and other eribulin analogs with modified side chains on position C32 of eribulin. In addition, there is a need in the art for a process for preparation of (3R)-2,4-diiodo-3-methylbut-1-ene (7a), and its analogs (7), that can be prepared from commercially available starting material. Moreover, there is a need in the art for a process for the preparation of (3R)-2,4-diiodo-3-methylbut-1-ene (7a), and its analogs (7), that lead to (3R)-2,4-diiodo-3-methylbut-1-ene (7a), and its analogs (7), in high enantiomeric excess. In addition, there is a need in the art for a process for preparation of (3R)-2,4-diiodo-3-methylbut-1-ene (7a), and its analogs (7), where the process is scalable.

SUMMARY OF THE INVENTION

In one aspect, the specification discloses a process for the preparation of a compound of formula 7,

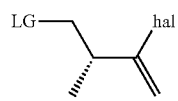

where LG is a leaving group, and hal is a halide and is Cl, Br or I;

the process comprising:

conversion of a compound of formula 4 to form a compound of formula 5, where PG is a protecting group and hal is as defined above;

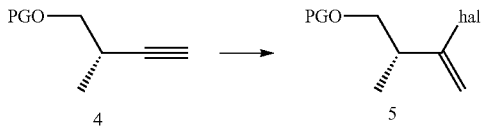

deprotecting the compound of formula 5 to form the compound of formula 6; and

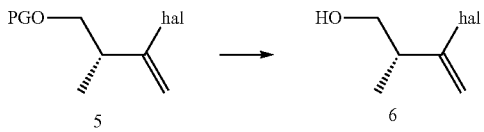

converting or substituting the hydroxyl group of the compound of formula 6 to a leaving group LG, to form the compound of formula 7

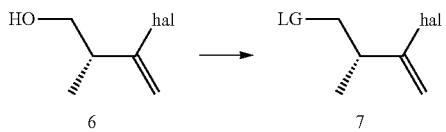

wherein, LG is as defined above.

In another aspect, the specification discloses a compound of formula 8

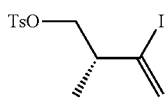

wherein Ts is tosylate $CH_3C_6H_4SO_2$.

DESCRIPTION

As described above, in one aspect the specification relates to a process for the preparation of a compound of formula 7,

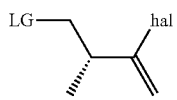

where LG is a leaving group, and hal is a halide and is Cl, Br or I;

the process comprising:

conversion of a compound of formula 4 to form a compound of formula 5, where PG is a protecting group and hal is as defined above;

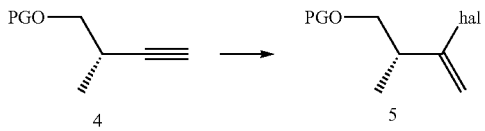

deprotecting the compound of formula 5 to form the compound of formula 6; and

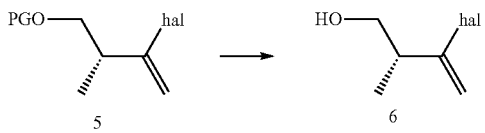

converting or substituting the hydroxyl group of the compound of formula 6 to a leaving group LG, to form the compound of formula 7

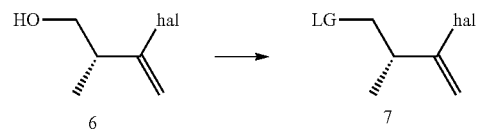

wherein, LG is as defined above.

The process for the conversion of a compound of formula 4 to a compound of formula 5 is not particularly limited, and can take place by the addition of a halide, where the halide is Cl, Br or I. Different reagents can be used for the addition of the halide to the alkyne, depending upon the protecting group and the overall synthetic scheme. The reagent used for addition of the halide to the alkyne is not particularly limited, and should also be known to a person of skill in the art or can be determined. In one embodiment, for example and without limitation, a hydrogen halide or a borane reagent is used for addition of the halide to the alkyne. In a further embodiment, for example and without limitation, the hydrogen halide is HCl, HBr or HI. In another embodiment, for example and without limitation, the borane reagent is B-iodo-9-borabicyclo[3.3.1]nonane (B—I-9-BBN) or B-bromo-9-borabicyclo[3.3.1]nonane (B—Br-9-BBN).

A leaving group as disclosed herein is a molecular fragment or stable species that can be detached from a molecule in a bond-breaking step. The leaving group, in accordance with the specification, is not particularly limited and should be known to a person of skill in the art or can be determined. The ability of a leaving group to depart is correlated with the plc, of the conjugate acid, with lower plc, being associated with better leaving group ability. Examples of leaving group include, without limitation, halide or a sulfonate. Halides can include, for example, Cl, Br or I. Examples of sulfonates can include, without limitation, nonaflate, triflate, fluorosulfonate, tosylate, mesylate or besylate. In one embodiment, for example and without limitation, the leaving group is tosylate. In another embodiment, for example and without limitation, the leaving group is I.

The process for the conversion or substitution of the hydroxyl group of the compound of formula 6 to a leaving group, as described herein, to form the compound of formula 7, is not particularly limited, and should be known to a person of skill in the art or can be determined. In one embodiment, for example and without limitation, the hydroxyl group is converted into a leaving group by formation of, for example and without limitation, a sulfonate group. In another embodiment, for example and without limitation, the hydroxyl group undergoes substitution to form a leaving group, for example and without limitation, a halide.

In a further embodiment, the process for the conversion of the hydroxyl group into a sulfonate leaving group is not particularly limited, and should be known to a person of skill in the art or can be determined. In one embodiment, the hydroxyl group is converted into a tosylate. Scheme 1 discloses, as an embodiment, where the compound of formula 6a is reacted with tosyl chloride to form the compound of formula 8.

Scheme 1: Process for preparation of compound of formula 8.

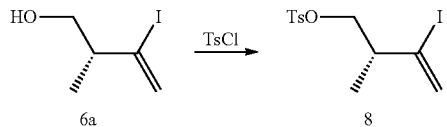

In another embodiment, the process for the substitution of the hydroxyl group into a leaving group is not particularly limited, and should be known to a person of skill in the art or can be determined. In one embodiment, the hydroxyl group is substituted by a halide, for example and without limitation, Cl, Br or I. Scheme 2 discloses, as an embodiment, where the compound of formula 6a is reacted with carbon tetraiodide and triphenylphosphine to form the compound of formula 7a.

Scheme 2: Process for preparation of compound of formula 7a.

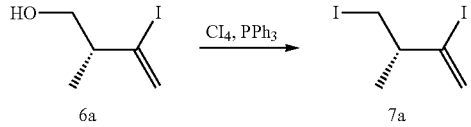

In one embodiment, the compound of formula 4 is formed from a compound of formula 3, where PG is as described herein. In a further embodiment, a Corey-Fuchs type reaction, Seyferth-Gilbert homologation or a Bestmann modification is carried out on the compound of formula 3 to form the compound of formula 4.

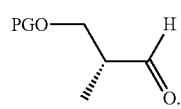

3

The Corey-Fuchs reaction, also known as the Ramirez-Corey-Fuchs reaction is known in the art. The reaction results in the conversion of an aldehyde into an alkyne (Scheme 3).

Without being bound to a particular theory, the reaction, generally involves reacting an aldehyde with carbon tetrabromide in the presence of triphenylphosphine (PPh$_3$) to form a dibromoalkene, which can undergo a metal-halogen exchange in the presence of a strong base, such as, for example and without limitation, butyl lithium. The reaction can then be quenched, for example and without limitation, with water or an alcohol to form an alkyne.

Scheme 3: The Corey-Fuchs reaction

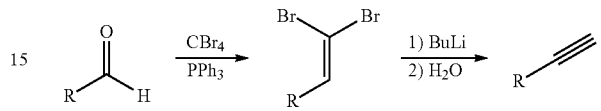

The Seyferth-Gilbert homologation or its Bestmann modification reactions are known in the art. These homologation reactions result in an increase of one additional carbon unit to the starting material, and similar to the Corey-Fuchs reactions, converts an aldehyde to an alkyne.

The Seyferth-Gilbert homologation reaction is shown in Scheme 4 (reaction shown for a ketone), and involves use of dimethyl(diazomethyl)phosphonate. The Bestmann modification (Scheme 5) of the reaction involves use of dimethyl-1-diazo-2-oxopropylphosphonate that yields dimethyl(diazomethyl)phosphonate in situ.

Scheme 4: A representative Seyferth-Gilbert homologation reaction.

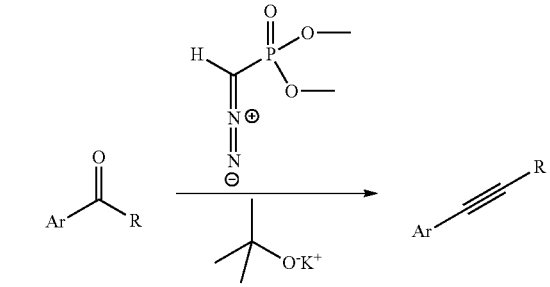

Scheme 5: A representative Bestmann modification of the Seyferth-Gilbert homologation reaction.

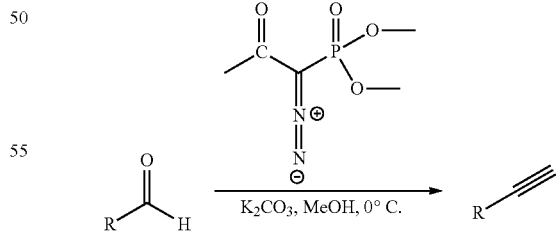

In an embodiment, modifications of the Corey-Fuchs, Seyferth-Gilbert or the Bestmann modification reaction can be used to carry out the reaction, so long as the reaction results in the formation of the alkyne. In a further embodiment, other reactions may be used to convert an aldehyde, ketone, ester, anhydride, ester or other analogs into the desired alkyne. In a still further embodiment, the compound of formula 3 is reacted with dimethyl-1-diazo-2-oxopropylphosphonate to form the compound of formula 4.

In one embodiment, the compound of formula 3 can be prepared, as shown in Scheme 6, from the compound of formula 1. In a further embodiment, the compound of formula 1 is a (R)-(−)-3-hydroxy-2-methylpropionic acid methyl ester (Roche ester) 1a (where R is methyl) that can be commercially available in high enantiomeric purity (ca. 99.9% e.e.) or can be prepared. The use of a high enantiomeric purity of a starting material can help to obtain the compound of formula 3, and from thereon, the compound of formula 7, in high enantiomeric excess. In one embodiment, for example and without limitation, the enantiomeric purity of any one of the compounds of formula 2 to 8 is about 99.0%, 99.1%, 99.2%, 99.3% 99.4%, 99.5%, 99.6%, 99.7%, 99.8%, 99.9% e.e. or any values in between.

As shown in Scheme 6, the process involves protecting the hydroxyl group of the compound of formula 1 to form the compound of formula 2, followed by reducing the carbonyl carbon of the compound of formula 2 to form the compound of formula 3.

Scheme 6: Process for formation of compound 3 from compound 1.

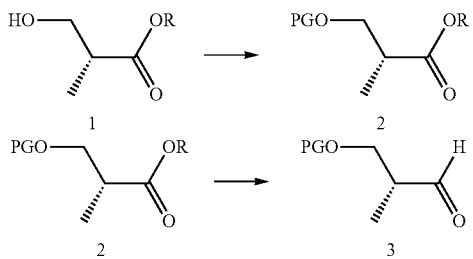

The R group in the compound of formula 1 is not particularly limited, and should be known to a person of skill in the art or can be determined. In one embodiment, the R group is an alkyl group or an aryl group. The length of the alkyl group or the number of atoms in the alkyl group or the aryl group are not particularly limited, and should be known to a person of skill in the art or can be determined. In one embodiment, for example and without limitation, the alkyl group is a $C_{1-6}$ alkyl. In another embodiment, for example and without limitation, the aryl group is a $C_{6-14}$ aryl.

The term $C_{1-6}$ alkyl in accordance with the specification is not particularly limited and should be known to a person of skill in the art. The $C_{1-6}$ alkyl may be, for example, and without limitation, any straight or branched alkyl, for example, methyl, ethyl, n-propyl, i-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl or 3-methylpentyl.

The term aryl in accordance with the specification is not particularly limited and should be known to a person of skill in the art. The term "aryl" refers to aromatic groups which have at least one ring having a conjugated-electron system and includes carbocyclic aryl, heterocyclic aryl (also known as heteroaryl groups) and biaryl groups, all of which may be optionally substituted. The aryl groups can include, for example and without limitation, six to fourteen atoms. Examples of aryl group can include, without limitation, phenyl, pyridyl or naphthyl.

The protecting group (PG) as described herein and used to protect the hydroxyl group of the compound of formula 1 is not particularly limited and should be known to a person of skill in the art or can be determined. In one embodiment, the protecting group used is, for example and without limitation, an ether-based or a silyl-based protecting group.

In a further embodiment, the ether-based protecting group is, for example and without limitation, benzyl (Bn), 2-methoxyethoxymethyl (MEM), trityl (Tr), monomethoxytrityl (MMT), dimethoxytrityl (DMT), methoxymethyl (MOM), p-methoxybenzyl (PMB) or tetrahydropyranyl (THP). Process for removing ether-based protecting groups is not particularly limited, and should be known to a person of skill in the art or can be determined. In one embodiment, for example and without limitation, ether-based protecting groups can be removed by use of an acid-deprotection step or by hydrogenation.

In another embodiment, the silyl-based protecting group is, for example and without limitation, tert-butyldimethylsilyl (TBDMS), tri-iso-propylsilyloxymethyl (TOM), triisopropylsilyl (TIPS) or tert-butyldiphenylsilyl (TBDPS). In a still further embodiment, the protecting group is tert-butyldiphenylsilyl (TBDPS). Process for removing silyl-based protecting groups is not particularly limited, and should be known to a person of skill in the art or can be determined. In one embodiment, for example and without limitation, silyl-based protecting groups are removed by use of a fluoride source. The fluoride source is not particularly limited, and should be known to a person of skill in the art or can be determined. In a further embodiment, the fluoride source is, for example and without limitation, sodium fluoride (NaF), tetra-n-butylammonium fluoride (TBAF), pyridinium hydrofluoride (HF-Py) or triethylammonium fluoride (HF-NEt$_3$).

The reduction of the ester of formula 2 can be carried out using a reducing agent, which should be known to a person of skill in the art or can be determined. The reducing agents used in accordance with the specification are not particularly limited. In one embodiment, for example and without limitation, the reducing agent provides a hydride ion to the carbon atom of the carbonyl group in the compound of formula 2. In a further embodiment, the reagent used to provide the hydride ion is, for example and without limitation, diisobutylaluminum hydride (DIBAL) or sodium aluminum hydride (NaAlH$_4$).

As noted above, in another aspect, the specification relates to a compound of formula 8, wherein Ts is a tosylate $CH_3C_6H_4SO_2$

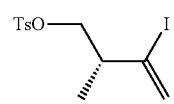

In one embodiment, the overall process for the preparation of compounds of formula 7a and 8, starting from the compound of formula 1 is as shown in Scheme 7.

Scheme 7: An embodiment for the process of preparation of compound of formula 7a and 8 from compound of formula 1a (Roche ester).

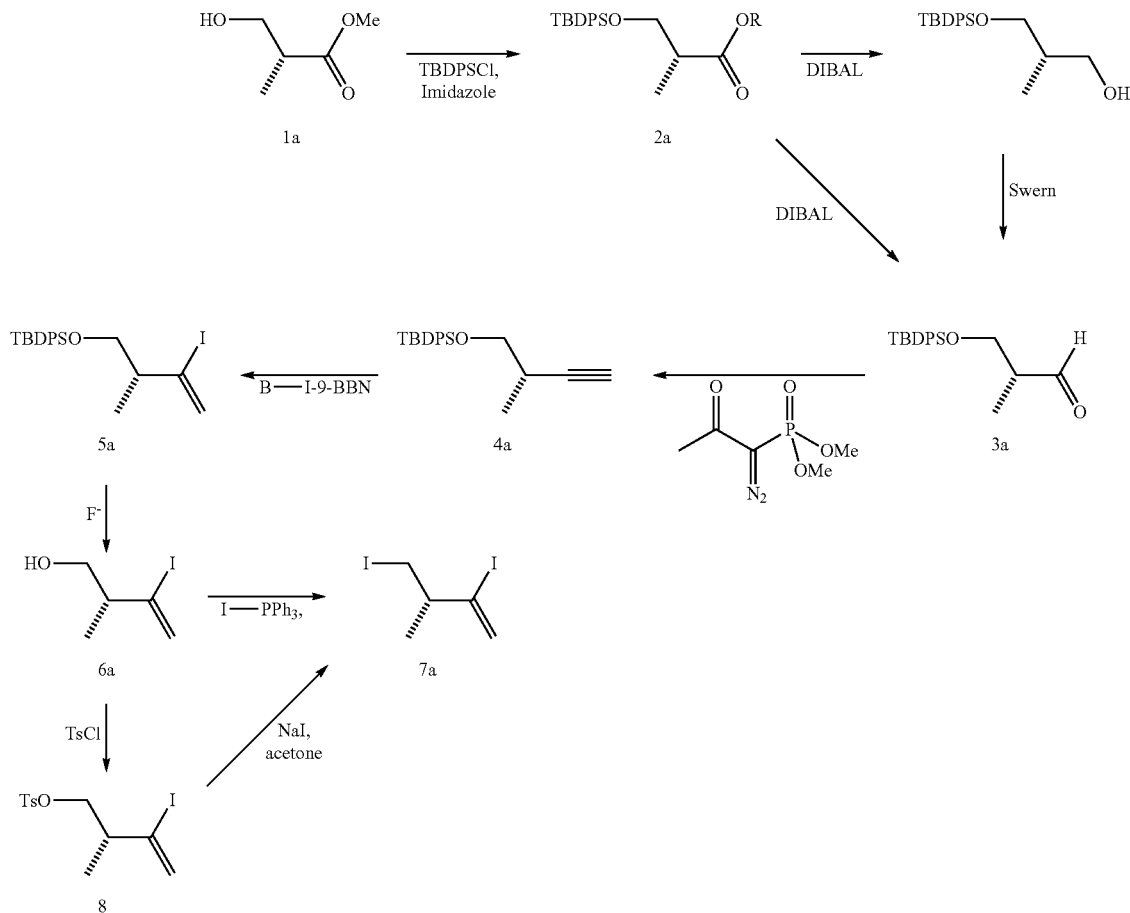

Scheme 7 discloses, in an embodiment, the process for preparation of compounds of formula 7a and 8 (compound 8 is a specific embodiment of the compound of formula 7) starting from the (R)-(−)-3-hydroxy-2-methylpropionic acid methyl ester (Roche ester) 1a, which can be commercially available in high enantiomeric excess. The use of 1a can help in obtaining compounds of formula 7 in high enantiomeric excess, using the process as described herein.

In brief, the hydroxyl group of the Roche ester 1a is protected with a silyl-protecting group, such as tert-butyldiphenylsilyl (TBDPS) using tert-butyldiphenylsilyl chloride (TBDPSCl) to form the compound of formula 2a. Reduction of the protected ester 2a with a hydride source, such as diisobutylaluminum hydride (DIBAL) can lead to, depending upon the conditions and reagents used, the 1,3-mono-protected alcohol or the compound of formula 3a. The 1,3-mono-protected can be oxidized, for instance by Swern oxidation to form the compound of formula 3a. The protected aldehyde 3a can be converted to the alkyne 4a, using conditions as disclosed herein, followed by addition of the halide, such as I, to form the compound of formula 5a. Using a fluoride source, the compound of formula 5a is desilylated to form the compound of formula 6a. To form the compound of formula 7a, the compound of formula 6a can be reacted with I—PPh₃ (that can be formed from I₂, PPh₃). Alternatively, the compound of formula 6a can be reacted with tosyl chloride (TsCl) to form the compound of formula 8.

EMBODIMENTS

1. A process for the preparation of a compound of formula 7,

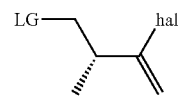

where LG is a leaving group, and hal is a halide and is Cl, Br or I;
the process containing:
conversion of a compound of formula 4 to form a compound of formula 5, where PG is a protecting group and hal is as defined above;

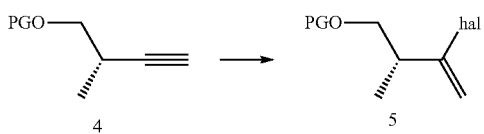

deprotecting the compound of formula 5 to form the compound of formula 6; and

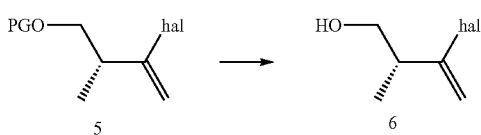

converting or substituting the hydroxyl group of the compound of formula 6 to a leaving group LG, to form the compound of formula 7

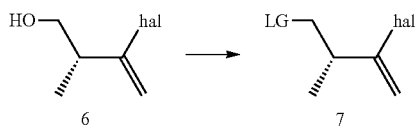

wherein, LG is as defined above.

2. The process according to embodiment 1, wherein the compound of formula 4 is formed from a compound of formula 3

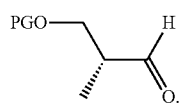

3. The process according to embodiment 2, wherein a Corey-Fuchs type reaction, Seyferth-Gilbert homologation or a Bestmann modification is carried out on the compound of formula 3 to form the compound of formula 4.

4. The process according to embodiment 2 or 3, wherein the compound of formula 3 is reacted with dimethyl-1-diazo-2-oxopropylphosphonate to form the compound of formula 4.

5. The process according to any one of embodiments 2 to 4, wherein the compound of formula 3 is formed by
  protecting the hydroxyl group of the compound of formula 1, wherein R is an alkyl or an aryl group, to form the compound of formula 2; and

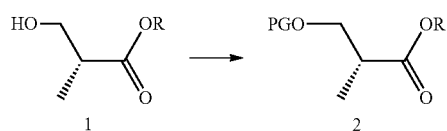

reducing the carbonyl carbon of the compound of formula 2 to form the compound of formula 3

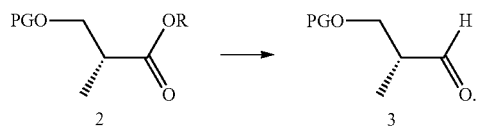

6. The process according to embodiment 5, wherein R is methyl.

7. The process according to embodiment 5 or 6, wherein the reduction reaction is carried out using a hydride source.

8. The process according to embodiment 7, wherein the hydride source is diisobutylalumium hydride (DIBAL).

9. The process according to any one of embodiments 1 to 8, wherein the compound of formula 4 is reacted with B—I-9-BBN or B—Br-9-BBN to form the compound of formula 5.

10. The process according to any one of embodiments 1 to 9, wherein LG is a halide.

11. The process according to embodiment 10, wherein the halide is I.

12. The process according to any one of embodiments 1 to 11, wherein LG is a sulfonate-based leaving group.

13. The process according to embodiment 12, wherein the sulfonate-based leaving group is nonaflate, triflate, fluorosulfonate, tosylate, mesylate or besylate.

14. The process according to embodiment 12 or 13, wherein the leaving group is a tosylate.

15. The process according to any one of embodiments 1 to 14, wherein PG is an ether-based or a silyl-based protecting group.

16. The process according to embodiment 15, wherein the silyl-based protecting group is tert-butyldimethylsilyl (TBDMS), tri-iso-propylsilyloxymethyl (TOM), triisopropylsilyl (TIPS) or tert-butyldiphenylsilyl (TBDPS).

17. The process according to embodiment 15 or 16, wherein the silyl-based protecting group is tert-butyldiphenylsilyl (TBDPS).

18. The process according to embodiment 15, wherein the ether-based protecting group is benzyl (Bn), 2-methoxyethoxymethyl (MEM), trityl (Tr), monomethoxytrityl (MMT), dimethoxytrityl (DMT), methoxymethyl (MOM), p-methoxybenzyl (PMB) or tetrahydropyranyl (THP).

19. The compound of formula 8

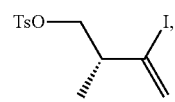

wherein Ts is a tosylate $CH_3C_6H_4SO_2$.

20. A compound of formula 7,

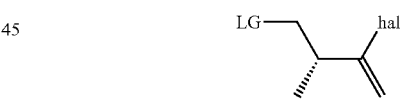

where LG is a leaving group, and hal is a halide and is Cl, Br or I, having an enantiomeric excess of 99% or greater.

21. The compound according to embodiment 20, wherein LG is a halide or a sulfonate-based leaving group.

22. The compound according to embodiment 20 or 21, wherein the halide is Cl, Br or I.

23. The compound according to embodiment 20 or 21, wherein the halide is I.

24. The compound according to embodiment 20 or 21, wherein the sulfonate-based leaving group is nonaflate, triflate, fluorosulfonate, tosylate, mesylate or besylate.

25. The compound according to embodiment 20 or 21, wherein the sulfonate-based leaving group is tosylate.

26. The compound according to any one of embodiments 20 to 25, wherein the enantiomeric excess (ee) is 99.9%.

27. A process for the preparation of Halichondrin B or its derivatives, comprising the method as defined in any one of embodiments 1-18.

28. A process for the preparation of Halichondrin B or its derivatives, comprising reacting the compound as defined in any one of claims 20 to 26.

EXAMPLES

The following examples are illustrative and non-limiting, and represent specific embodiments of the present invention.

Example 1

Preparation of compound 2a (where PG is TBDPS and R is Me)

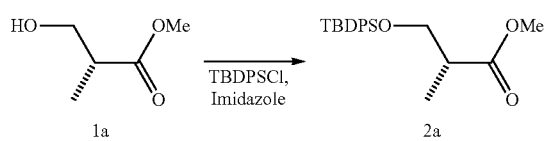

A solution of ester 1a (25.0 g) in 235 mL dichloromethane was stirred magnetically under nitrogen in a 1 L three-necked round bottomed flask. To this solution was added 18.7 g of imidazole and the resultant mixture stirred until all contents had completely dissolved. The resultant clear colorless solution was then cooled in an ice bath to 5° C., after which 55 mL of neat tert-butyldiphenylsilylchloride (TBDPSCl, 58.2 g, 211.6 mmol, 1.0 equivalents) was added in two portions (30 mL and 25 mL) over 15 minutes. The solution was observed to haze gradually, and then grow cloudy with a white crystalline suspended precipitate. Thin layer chromatography (TLC) analysis (10% v/v EtOAc in heptane, AMCS and $KMnO_4$ stains) showed disappearance of TBDPSCl after 90 minutes, and an NMR of an aliquot showed disappearance of compound 1a after this time. After 2 hours 200 mL of 5% w/w aqueous sodium bicarbonate solution was added to the round-bottomed flask and allowed to stir at room temperature for 15 minutes, after which the mixture was separated, and the aqueous layer extracted with 100 mL dichloromethane. The organics were then combined and washed with 2×200 mL brine, dried over sodium sulfate, filtered and concentrated under reduced pressure to give 2a as a light yellow oil (74.05 g, 98% yield).

Example 2

Preparation of Compound 2a (where PG is TBDPS and R is Me)

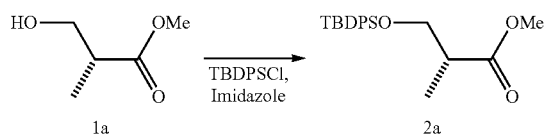

A solution of ester 1a (211 g) in dichloromethane (1.5 L) was cooled to −20° C., after which imidazole (159 g) was added. Once all reagents had dissolved, neat tert-butyldiphenylsilylchloride (520 g) was added dropwise, keeping the reaction temperature below 0° C. The reaction was allowed to warm up to room temperature and, after agitating overnight, it was quenched with ice-cold water (600 mL). The layers were separated, and the organic phase was dried over $MgSO_4$, filtered and concentrated under reduced pressure to give crude compound 2a (690 g) as a yellow oil, which was directly used in the next step without any further purification.

Example 3

Reduction of 2a to Form 3a

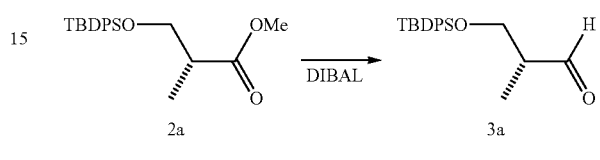

A solution of ester 2a (20.0 g) in dichloromethane (300 mL) was cooled to −70° C., after which a solution of diisobutylaluminum hydride (1M in dichloromethane, 68 mL) was added dropwise so that the temperature of the reaction did not exceed −65° C. during the addition. After agitating for 1 h, methanol (2.7 mL) was added all at once, and the solution was allowed to warm to room temperature. A saturated aqueous solution of sodium potassium tartrate (300 mL) was added, and the biphasic mixture was vigorously agitated for another hour. The layers were separated, and the aqueous phase extracted 3 times with dichloromethane (50 mL). The combined organic extracts were washed with brine (100 mL), dried over sodium sulfate, filtered and concentrated under reduced pressure to give the desired aldehyde 3a (17.4 g) as a thick, clear, colorless oil, which was directly used in the next step without any further purification.

Example 4

Formation of Compound 3a

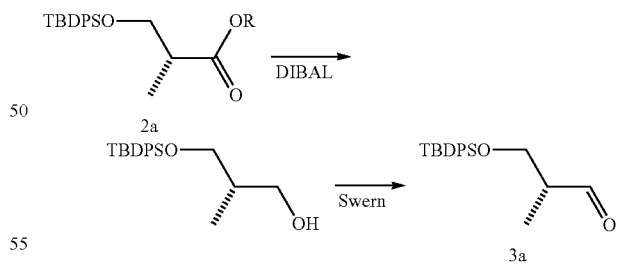

A solution of compound 2a (200 g) in dichloromethane (2.0 L) was cooled to −70° C., after which a solution of diisobutylaluminum hydride (1M in dichloromethane, 1.18 L) was added dropwise so that the temperature of the reaction did not exceed −60° C. The reaction mixture was allowed to warm up to −20° C. and was then quenched by dropwise addition of aqueous pH 7 buffer solution (270 mL).

After agitating overnight, the reaction mixture was filtered, and the residue washed with dichloromethane (1.0 L). The combined filtrates were concentrated under reduced pressure to give the desired alcohol (176 g) as a light yellow oil, which was dissolved dichloromethane (1.0 L) to form Solution A.

A solution of oxalyl chloride (70 mL) in dichloromethane (1.6 L) was cooled to −70° C., after which DMSO (76 mL) was added dropwise so that the temperature of the reaction did not exceed −60° C. After 20 min. agitation, Solution A was added dropwise so that the temperature of the reaction did not exceed −55° C. The reaction mixture was agitated for 30 min. and triethylamine (374 mL) was then added, also dropwise to ensure that the temperature of the reaction did not exceed −55° C. The reaction was agitated for 2 h at −60° C., then warmed up to −40° C. and quenched by addition of saturated aqueous ammonium chloride solution (1.0 L) and water (1.0 L). The phases were separated and the organic layer was sequentially washed with water (1.3 L) and brine (1.3 L), then concentrated under reduced pressure to give aldehyde 3a (183 g) as a yellow oil, which was directly used in the next step without any further purification.

Example 5

Formation of Alkyne of Formula 4a

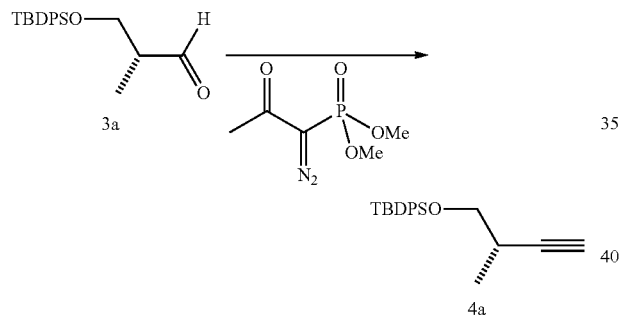

A solution of (1-diazo-2-oxo-propyl)-phosphonic acid dimethyl ester (13.0 g, 67.6 mmol) in anhydrous tetrahydrofuran (235 mL) was cooled to −70° C. while being magnetically stirred under nitrogen. Then 135.3 ml of a 0.5 M solution of sodium methoxide in methanol was added dropwise to the stirred solution over 30 minutes. After addition was complete a solution of the aldehyde 3a (9.2 g, 28.2 mmol) in anhydrous tetrahydrofuran (134 mL) was added dropwise to the stirred solution over 30 minutes. After addition was complete the resulting solution was permitted to slowly warm to room temperature over a period of 30 minutes, after which it was stirred at room temperature for 16 hours. TLC analysis at this point showed presence of product. The stirred solution was quenched with 100 mL 5% w/w aqueous NaHCO₃ solution and then concentrated under reduced pressure to ~50% of its original volume by visual inspection. This mixture was then extracted 6×50 mL methyl tert-butyl ether (MTBE). The organic extracts were combined, washed with 200 mL brine, dried over Na₂SO₄, filtered and concentrated under reduced pressure to give 8.4 g of crude product. This was then chromatographed on silica gel using 5% v/v ethyl acetate in heptane to give 8.0 g (88% yield) of pure product 4a.

Example 6

Formation of Alkyne of Formula 4a

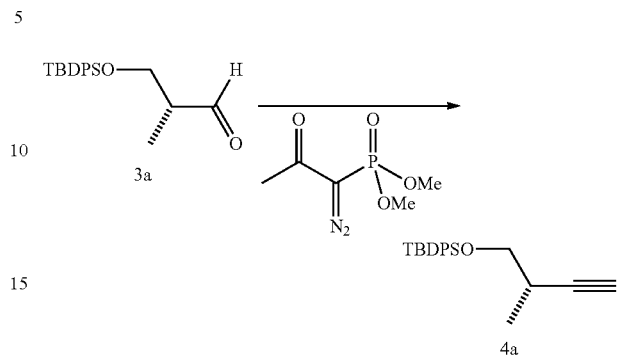

A solution of (1-diazo-2-oxo-propyl)-phosphonic acid dimethyl ester (248 g) in tetrahydrofuran (2.0 L) was cooled to −70° C., and a mixture of NaOMe solution (25% w/w in MeOH, 295 mL) and anhydrous methanol (300 mL) was added dropwise, keeping the reaction temperature below −60° C. The reaction was agitated at −70° C. for 1 h, after which a solution of the aldehyde 3a (183 g) in tetrahydrofuran (700 mL) was added dropwise, keeping the reaction temperature below −60° C. The resulting reaction mixture was allowed to slowly warm to 10° C., after which it was quenched with a mixture of saturated aqueous NaHCO₃ (700 mL) and water (1.4 L). After dilution with tert-butyl methyl ether (1.4 L), the layers were separated and the aqueous phase was extracted once with tert-butyl methyl ether (1.4 L). The combined organic layers were washed twice with brine (1.4 L), concentrated under reduced pressure and applied to a silica gel pad (150 g). Elution with heptane followed by concentration under reduced pressure gave alkyne 4a (141 g) as colorless oil.

Example 7

Formation of Compound 5a, where Hal is I

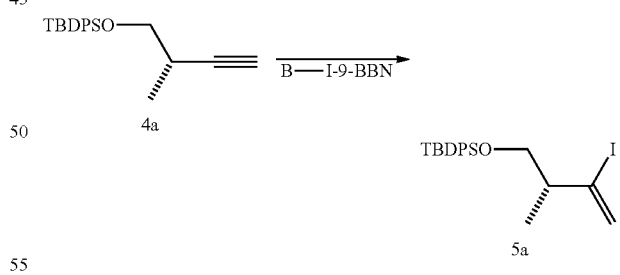

A solution of 4a (2.0 g, 3.1 mmol) in 40 mL heptane was cooled to −20° C. in a dichloroethane/dry ice bath with magnetic stirring under nitrogen. To this solution was added dropwise 7.4 mL (1.2 eq) of a 1M solution of B-iodo-9-borabicyclo[3.3.1]nonane (B—I-9-BBN) in hexanes over ten minutes. The solution was then allowed to warm to 0° C. by replacement of the cooling bath to one with ice. After 1 hour an aliquot was collected and treated with acetic acid. NMR analysis of the aliquot showed presence of the desired product and disappearance of the starting material. After 90 minutes 2.4 mL of neat glacial acetic acid was added to the solution, which was allowed to stir at 0° C. for 1 hour. The resulting solution was then allowed to warm to room temperature over 30 minutes before 100 mL of 5% w/w aqueous sodium bicarbonate was slowly added to the reaction mixture, and then placed in a separatory funnel, washed with 100 mL of 1M aqueous sodium thiosulphate solution, washed with 100 mL brine, dried over sodium sulphate, filtered and concentrated under reduced pressure to give 4.0 g of a pale yellow oil. This oil was chromatographed on silica gel using 5% v/v ethyl acetate solution in heptane to give 2.6 g (94% yield) of product 5a.

Example 8

Formation of Compound 5a, where Hal is I

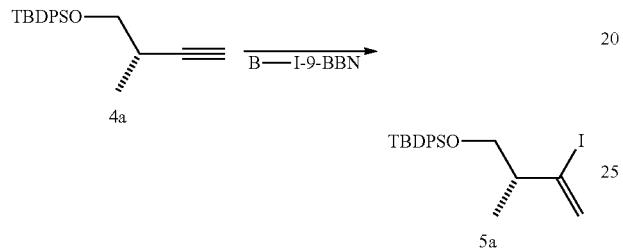

A solution of 4a (140 g) in heptane (2.8 L) was cooled to −40° C. and a solution of B-iodo-9-borabicyclo[3.3.1]nonane (1M in hexanes, 520 mL) was added dropwise, keeping the reaction temperature below −30° C. The reaction was further agitated for 1 h, after which glacial acetic acid (37 mL) was added to the solution dropwise, keeping the reaction temperature below −15° C. The resulting reaction mixture was allowed to warm to 0° C., and was then quenched with an aqueous solution of NaHCO$_3$ (72 g) in water (1.4 L). The phases were separated and the organic layer was sequentially washed with water (1.5 L) and brine (1.0 L), then concentrated under reduced pressure. The residue (274 g) was dissolved in heptane (500 mL) and applied to a silica gel column (500 g). Elution with heptane gave iodide 5a (185 g) as a colorless oil.

Example 9

Formation of Compound 6a and its Conversion to Compound 8

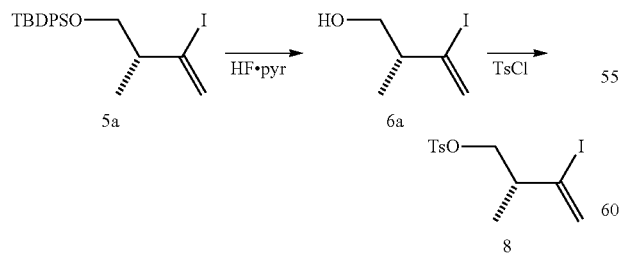

To a cooled solution of 5a (1 g) in dichloromethane (5 mL) was added a solution of hydrogen fluoride in pyridine (70% w/w, 0.6 mL). The reaction mixture was then allowed to warm slowly to room temperature, and agitated for 18 hours. The reaction mixture was quenched with aqueous NaHCO$_3$ solution (5% w/w, 10 mL), the phases were separated and the organic layer was washed with brine (10 mL), dried over Na$_2$SO$_4$ and filtered. To the filtrate was then added of p-toluenesulfonyl chloride (0.64 g), triethylamine (0.38 mL), and 4-dimethylaminopyridine (0.07 g). The reaction was heated for 16 hours, after which it was diluted with dichloromethane (10 mL), then sequentially washed with aqueous HCl (1M, 10 mL), twice with aqueous sodium bicarbonate (5% w/w, 10 mL) and brine (10 mL). After drying sodium sulphate, the organic layer was filtered, concentrated under reduced pressure and chromatographed on silica gel using 5% v/v ethyl acetate in heptane as the eluent to give compound 8 (0.5 g).

Example 10

Formation of Compound 6a

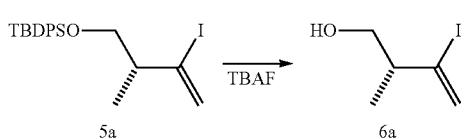

A solution of compound 5a (185 g) in tetrahydrofuran (925 mL) was cooled to 5° C., after which a solution of tetrabutylammonium fluoride (1M in tetrahydrofuran, 452 mL) was added dropwise so that the temperature of the reaction did not exceed 10° C. The reaction was warmed up to room temperature and agitated for 4 h, after which it was quenched with saturated aqueous ammonium chloride solution (60 mL). The layers were separated and the organic phase was concentrated under reduced pressure. The residue was applied to a silica gel column (870 g) and eluted with a gradient 0-20% v/v ethyl acetate in cyclohexane, followed by another gradient 10-20% v/v ethyl acetate in dichloromethane. All product containing fractions were concentrated under reduced pressure and the residue was applied to another silica gel column (100 g) and eluted with a gradient 20-67% v/v dichloromethane in cyclohexane, giving the desired alcohol 6a (79 g) as a light yellow oil.

Example 11

Formation of Compound 7a, where LG and Hal are Both I

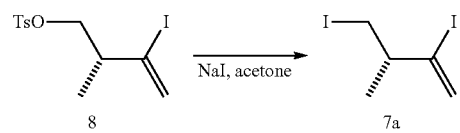

To a solution of 8 (0.075 g) in acetone (1 mL) was added sodium iodide (0.124 g). The reaction mixture was agitated at 50° C. for 16 hours, after which it was diluted with pentane (10 mL). The resulting suspension was filtered and the residue rinsed with pentane. The combined filtrates were sequentially washed with 1M aqueous sodium thiosulphate solution and brine, then dried over Na$_2$SO$_4$, filtered and concentrated under atmospheric pressure. The residue was chromatographed using heptane as the eluent to give of compound 7a as a light pink oil (0.054 g).

Example 12

Formation of Compound 7a

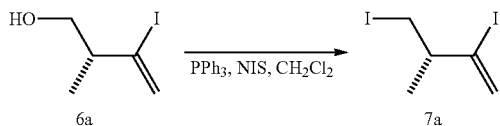

A solution of compound 6a (2.0 g) and triphenylphosphine (2.72 g) in dichloromethane (45 mL) was cooled to 5° C. and solid N-iodosuccinimide (NIS, 2.33 g) was added in portions so that the temperature of the reaction did not exceed 10° C. The reaction was warmed up to room temperature and agitated overnight, after which it was quenched with water (40 mL). The phases were separated and the organic layer was washed twice with water (40 mL) and concentrated under reduced pressure. The residue was suspended in cyclohexane (40 mL), filtered and the filtrate was concentrated under reduced pressure and the resulting oil was applied to a silica gel column (12 g) and eluted with cyclohexane to give compound 7a (1.7 g) as a colorless liquid.

Example 13

Formation of Compound 7a

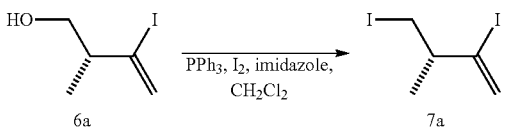

To a solution of compound 6a (20.0 g) and triphenylphosphine (29.7 g) in toluene (400 mL) was mixed with a solution of imidazole (15.4 g) in acetonitrile (100 mL) and to the resulting mixture was added solid iodine (28.7 g), in portions so that the temperature of the reaction did not exceed 30° C. The resulting suspension was warmed up to 55° C. and agitated at that temperature until the reaction was complete. The reaction mixture was washed twice with water (400 mL), followed by 10% w/w aqueous sodium thiosulphate solution (200 mL) and brine (400 mL). The organic phase was concentrated under reduced pressure and the residue was suspended in cyclohexane (400 mL). The mixture was filtered, the solids washed with cyclohexane (200 mL) and the combined filtrates were concentrated under reduced pressure. The residue was applied to a silica gel column (100 g) and eluted with cyclohexane to give compound 7a (21.2 g) as a colorless liquid.

Example 14

Formation of Compound 9a

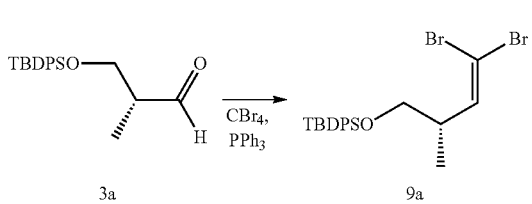

A solution of triphenylphosphine (4.31 g) in anhydrous dichloromethane (5.5 mL) was cooled to −10° C. and a solution of carbon tetrabromide (2.72 g) in anhydrous dichloromethane (2.05 mL) was added in one portion. After the solution returned to −10° C., a solution of compound 3a (1.34 g) in anhydrous dichloromethane (3.15 mL) was added dropwise. The reaction mixture was agitated for 4 hours at −10° C., after which it was quenched with aqueous NaHCO$_3$ solution (5% w/w, 10 mL). The phases were separated, and the organic layer was sequentially washed with water (10 mL) and brine (10 mL), then dried over Na$_2$SO$_4$, filtered and concentrated under reduced pressure. The residue was chromatographed on silica gel, using as eluent a gradient 0-5% v/v ethyl acetate in heptane, to give compound 9a (1.3 g).

Example 15

Formation of Compound 4a

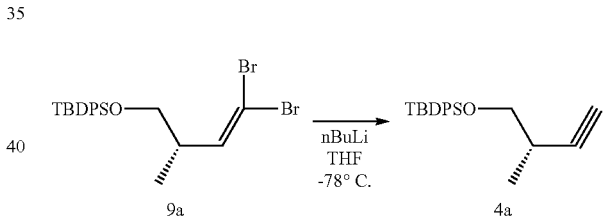

To a stirred solution of compound 9a (1.0 g) in anhydrous tetrahydrofuran cooled to −70° C. in a dry ice/acetone bath was added dropwise a solution of n-butyllithium 2.5M in hexane, 2.1 mL. The reaction was agitated at −70° C. for 90 minutes, after which it was warmed up to 0° C. and quenched with saturated aqueous ammonium chloride solution (5 mL). The reaction mixture was diluted with heptane (50 mL), and sequentially washed with 5% w/w aqueous sodium bicarbonate solution (100 mL) and brine (100 mL). The organic phase was dried over sodium sulphate, filtered and concentrated under reduced pressure to give a clear colorless oil (0.9 g). This was then chromatographed on silica gel, using as eluent a gradient 5-40% v/v ethyl acetate in heptane, to yield compound 4a (0.52 g).

Certain adaptations and modifications of the described embodiments can be made. Therefore, the above discussed embodiments are considered to be illustrative and not restrictive.

What is claimed is:
1. A process for the preparation of a compound of formula 7,

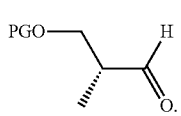

wherein: LG is a leaving group, and hal is a halide selected from the group consisting of Cl, Br or I; the process comprising:
converting of a compound of formula 4 to form a compound of formula 5, where PG is a protecting group and hal is as defined above;

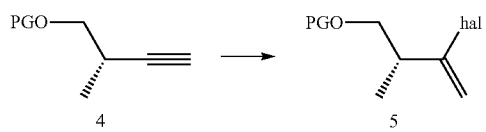

deprotecting the compound of formula 5 to form a compound of formula 6; and

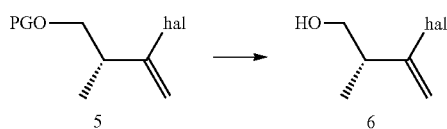

converting or substituting the hydroxyl group of the compound of formula 6 to a leaving group LG, to form the compound of formula 7

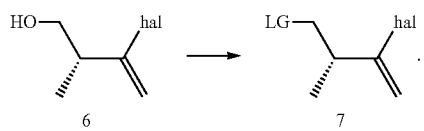

2. The process according to claim 1, further comprising forming the compound of formula 4 from a compound of formula 3

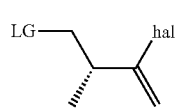

3. The process according to claim 2, wherein forming the compound of formula 4 comprises carrying out a Corey-Fuchs type reaction, Seyferth-Gilbert homologation or a Bestmann modification on the compound of formula 3 to form the compound of formula 4.

4. The process according to claim 2, wherein forming the compound of formula 4 comprises reacting the compound of formula 3 with dimethyl-1-diazo-2-oxopropylphosphonate to form the compound of formula 4.

5. The process according to claim 2, wherein forming the compound of formula 3 comprises:
protecting the hydroxyl group of a compound of formula 1, wherein R is an alkyl or an aryl group, to form a compound of formula 2; and

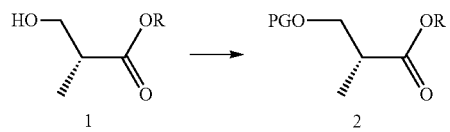

reducing the carbonyl carbon of the compound of formula 2 to form the compound of formula 3

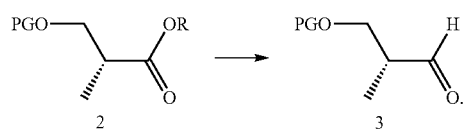

6. The process according to claim 5, wherein R is methyl.

7. The process according to claim 5, wherein reducing the carbonyl carbon reduction reaction is carried out using a hydride source.

8. The process according to claim 1, wherein converting the compound of formula 4 to the compound of formula 5 comprises reacting the compound of formula 4 is reacted with B-iodo-9-borabicyclo[3,3,1]nonane (B—I-9-BBN) or B-bromo-9-borabicyclo[3,3,1]nonane (B—Br-9-BBN) to form the compound of formula 5.

9. The process according to claim 1, wherein LG is a halide.

10. The process according to claim 1, wherein LG is a sulfonate-based leaving group.

11. The process according to claim 1, wherein PG is an ether-based or a silyl-based protecting group.

12. The process according to claim 11, wherein the silyl-based protecting group is tert-butyldimethylsilyl (TBDMS), tri-iso-propylsilyloxymethyl (TOM), triisopropylsilyl (TIPS) or tert-butyldiphenylsilyl (TBDPS).

13. The process according to claim 11, wherein the ether-based protecting group is benzyl (Bn), 2-methoxyethoxymethyl (MEM), trityl (Tr), monomethoxytrityl (MMT), dimethoxytrityl (DMT), methoxymethyl (MOM), p-methoxybenzyl (PMB) or tetrahydropyranyl (THP).

14. The compound of formula 8

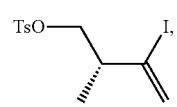

wherein Ts is a tosylate of the formula $CH_3C_6H_4SO_2$.

15. A compound of formula 7,

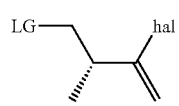

wherein:
LG is a sulfonate-based leaving group;
hal is a halide selected from the group consisting of Cl, Br or I; and
said compound has an enantiomeric excess of 99% or greater.

16. The compound according to claim 15, wherein LG is a tosylate of the formula $CH_3C_6H_4SO_2$, and the halide is Cl or Br a halide or a sulfonate based leaving group.

17. The compound according to claim 15, wherein the sulfonate-based leaving group is nonaflate, triflate, fluorosulfonate, tosylate, mesylate or besylate.

18. The compound according to claim 15, wherein the enantiomeric excess (ee) is 99.9%.

19. A process for the preparation of a halichondrin, comprising:
    converting a compound of formula 4 to form a compound of formula 5, where PG is a protecting group and hal is a halogen selected from the group consisting of Cl, Br, or I;

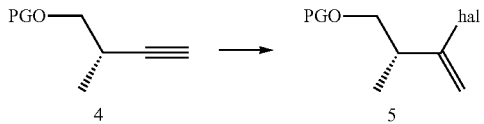

deprotecting the compound of formula 5 to form a compound of formula 6; and

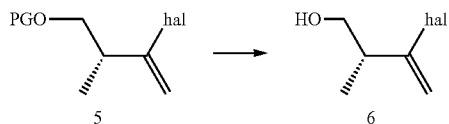

converting or substituting the hydroxyl group of the compound of formula 6 to a leaving group LG, to form the compound of formula 7

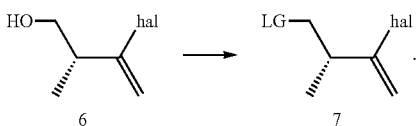

wherein: LG is a leaving group, and hal is defined as set forth above; and the method further comprises utilizing the compound of formula 7 as a building block in the synthesis of said halichondrin.

20. The process of claim 19, wherein:
    said compound of formula 7 has an enantiomeric excess of 99%; and
    in said compound of formula 7, LG is a sulfonate-based leaving group.

21. The process of claim 19, wherein said halichondrin is halichondrin B.

22. The process according to claim 19, wherein said halichondrin is Eribulin.

\* \* \* \* \*